(12) United States Patent
Ross et al.

(10) Patent No.: US 9,687,530 B2
(45) Date of Patent: Jun. 27, 2017

(54) METHOD OF TREATMENT OF HYPOXIA INDUCIBLE FACTOR (HIF)-RELATED CONDITIONS

(71) Applicant: Grifols Worldwide Operations Limited, Dublin (IE)

(72) Inventors: David A. Ross, Cary, NC (US); Ralph Christian Crumrine, Durham, NC (US)

(73) Assignee: Grifols Worldwide Operations Limited, Dublin (IE)

( * ) Notice: Subject to any disclaimer, the term of this patent is extended or adjusted under 35 U.S.C. 154(b) by 0 days.

(21) Appl. No.: 14/754,883

(22) Filed: Jun. 30, 2015

(65) Prior Publication Data

US 2016/0008437 A1 Jan. 14, 2016

Related U.S. Application Data

(60) Provisional application No. 62/023,446, filed on Jul. 11, 2014.

(51) Int. Cl.

| | | |
|---|---|---|
| *A61K 38/40* | (2006.01) | |
| *A61K 31/295* | (2006.01) | |
| *A61K 45/06* | (2006.01) | |
| *A61K 31/164* | (2006.01) | |
| *A61K 31/4704* | (2006.01) | |
| *A61K 31/16* | (2006.01) | |
| *A61K 31/198* | (2006.01) | |
| *A61K 31/4196* | (2006.01) | |
| *A61K 31/4412* | (2006.01) | |
| *A61K 31/223* | (2006.01) | |
| *A61K 31/426* | (2006.01) | |
| *A61K 31/472* | (2006.01) | |

(52) U.S. Cl.
CPC .............. *A61K 38/40* (2013.01); *A61K 31/16* (2013.01); *A61K 31/164* (2013.01); *A61K 31/198* (2013.01); *A61K 31/223* (2013.01); *A61K 31/4196* (2013.01); *A61K 31/426* (2013.01); *A61K 31/4412* (2013.01); *A61K 31/472* (2013.01); *A61K 31/4704* (2013.01); *A61K 45/06* (2013.01)

(58) Field of Classification Search
None
See application file for complete search history.

(56) References Cited

U.S. PATENT DOCUMENTS 5,110,722 A * 5/1992 Brockbank .......... A01N 1/0226
435/1.1

FOREIGN PATENT DOCUMENTS

WO WO 2006/020727 A2 2/2006
WO WO 2013/068504 A1 * 5/2013

OTHER PUBLICATIONS

De Vries et al., Transplantation, 77(5):669-675, Mar. 2004.*
Chen-Roetling et al., Neuropharmacology, 60(2-3):423-431, Epub Oct. 27, 2010.*
Chen et al., JASN, vol. 9 No. 1:77-84, Jan. 1, 1998.*
Klebanoff and Waltersdorph, J. Exp Med., 172:1293-1303, Nov. 1990.*
Clausi et al., ASN Neuro 2(5): e00048, published Nov. 19, 2010.*
Heikkinen et al., Scandanavian Cardiovascular Journal, 38:178-186, 2004.*
Nagel et al., J Cerebral Blood Flow and Metabolism, 31:132-143, published online Apr. 21, 2010.*
Hanson et al., J Pharmacology and Experimental Therapeutics, 330(3):679-686, 2009.*
Steere et al., J Inorg Biochem. 116C:37-44, Nov. 2012.*
Chen-Roetling et al., Neuropharmacology, 60(2-3):423-31 (2011).
Wang and Semenza, Blood 82(12):3610-15 (1993).
Hamed and ElMelegy, Italian Journal of Pediatrics, 36:39 pp. 1-10 (2010).
Liu et al., Acta Pharmacologica Sinica, 30:1071-80 (2009).
K. Norrby, J. Vascular Research, 41:293-304 (2004).
Rasheduzzaman et al., Chemical Society Reviews, 37:1308-19 (2008).
Zakharova et al., Biometals 25:1247-59 (2012).

* cited by examiner

*Primary Examiner* — Kimberly A. Ballard
*Assistant Examiner* — Stacey MacFarlane
(74) *Attorney, Agent, or Firm* — Dinsmore & Shohl LLP

(57) ABSTRACT

The present invention relates to methods of treatment of Hypoxia Inducible Factor (HIF)-related conditions, and in particular to methods of treatment of HIF-related conditions comprising the administration of a composition comprising transferrins.

13 Claims, 22 Drawing Sheets

B    Modified Bederson Score

| | Saline$_{Apo}$ | ApoTf | Saline$_{Holo}$ | HoloTf |
|---|---|---|---|---|
| Median | 2.0 | 2.0 | 2.0 | 2.0 |
| 5 percentile | 1.3 | 1.3 | 2.0 | 2.0 |
| 95 percentile | 2.0 | 2.0 | 2.85 | 2.0 |

General Behavioral Score

| | Saline$_{Apo}$ | ApoTf | Saline$_{Holo}$ | HoloTf |
|---|---|---|---|---|
| Median | 1.0 | 2.0 | 2.0 | 1.0 |
| 5 percentile | 1.0 | 1.0 | 1.0 | 1.0 |
| 95 percentile | 3.25 | 2.7 | 3.5 | 2.0 |

FIGURE 5B

METHOD OF TREATMENT OF HYPOXIA INDUCIBLE FACTOR (HIF)-RELATED CONDITIONS

CROSS REFERENCE TO RELATED APPLICATIONS

This application claims priority to U.S. Provisional Patent Application No. 62/023,446, filed Jul. 11, 2014, the contents of all of which are specifically incorporated herein by reference.

FIELD OF THE INVENTION

The present invention relates to methods of treatment of Hypoxia Inducible Factor (HIF)-related conditions, and in particular to methods of treatment of HIF-related conditions comprising the administration of a composition comprising transferrins.

BACKGROUND OF THE INVENTION

Protecting cells, and specially neurons, from damage caused by various factors, including stroke, neurodegenerative disease, traumatic injury, etc., is important for long-term recovery of cell or neuronal function. Therapeutic treatment of injured cells or neurons by single agents has advantages, but is often not sufficient to mobilize the complexity of molecules needed to help in restoring complete function.

Physiological response to protect neurons or other cells from hypoxic or ischemic events, or from oxidation, is often considered to be mediated by expression of genes that are up-regulated through the Hypoxia Inducible Factor (HIF) signaling pathway, a key regulatory pathway that is responsive to cellular insults. In the brain, up-regulation of neuroprotective molecules is believed to be a critical factor in protecting cells from irreparable damage. However, few available drugs are sufficiently able to prevent, restore or reduce damage to neurons and other tissues. Additionally they are often toxic, have short half-lives, or both. For example, the international patent application WO2006/20727 proposes the use of deferoxamine as neuroprotector agent against the harmful effects of reperfusion; however, the administration of deferoxamine poses problems due to its reduced half-life in plasma.

Transferrins are iron-binding blood plasma glycoproteins that control the level of free iron in biological fluids. Transferrins function as the main transporter of iron in the circulation where it exists in an iron-free apo-transferrin (ApoTf) form, as monoferric transferrin, or as diferric holo-transferrin (HoloTf). Typically, iron is bound to 30% of all transferrin binding sites in circulation. The neuroprotection function of ApoTf but not HoloTf has been disclosed by Chen-Roetling et al. (Chen-Roetling J., Chen L., and Regan R. F. *Neuropharmacology*, 2011; 60(2-3): 423-431), suggesting that ApoTf may mitigate the neurotoxicity of hemoglobin after intracerebral hemorrhage.

The present inventors have found that it may be possible to boost the neuroprotective properties of transferrin administration in patients by combining it with other iron chelating agents or with another iron-binding plasma protein, such as Apolactoferrin, which has been shown to increase HIF1-$\alpha$, protein levels in some tissues and have effects on plasma EPO levels (Zakharova E. T. et al. *Biometals* (2012) 25:1247-1259). Molecules with iron chelating abilities have been suggested to be HIF pathway activators by blocking the activity of prolyl hydroxylases.

Therefore, the present invention refers to a method of treatment of Hypoxia Inducible Factor (HIF)-related conditions comprising the administration of a composition comprising transferrin. The present invention also refers to a method of treatment of Hypoxia Inducible Factor (HIF)-related conditions wherein the administered composition further comprises a combination of a transferrin and an iron chelator.

As used herein, the term "transferrin" and its plural refers to ApoTf alone, or HoloTf alone or a mixture thereof.

BRIEF DESCRIPTION OF THE DRAWINGS

The present invention is further described with reference to the following drawings, in which:

FIG. 5B shows Modified Bederson and General Behavioral scores for rats intravenously treated with drug comprising majority of ApoTf or HoloTf.

DETAILED DESCRIPTION OF THE INVENTION

Figure 1:
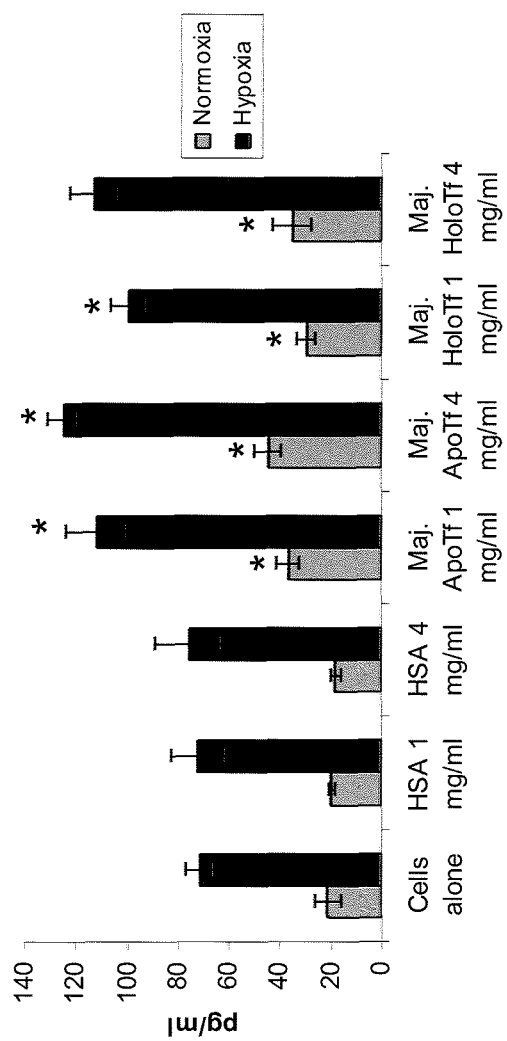
FIG. 1 shows that compositions of majority ApoTf and majority HoloTf induce HIF1 alpha protein under normoxic and hypoxic conditions 6 hrs post treatment.

In one aspect, the present invention refers to a method of treatment of Hypoxia Inducible Factor (HIF)-related conditions comprising the administration of a composition comprising transferrin. Preferably, transferrin is recombinant, plasma-derived or chemically synthesized transferrin.

When transferrin is recombinant, it can be obtained according to any technique known in the art of protein expression, production and purification. For example, nucleic acid sequence of transferrin can be inserted in any vector suitable for expression in the elected host cell, e.g. bacteria (*Escherichia coli, Bacilus subtilis, Salmonella typhimurium, Pseudomonas, Streptomyces* and *Staphylococcus*), yeast (*Saccharomyces, Pichia* or *Kuyveromyces* genus), insect cells (*Bombyx mori, Mamestra brassicae, Spodoptera frugiperda, Trichoplusia ni* or *Drosophila melanogaster*) or mammalian cells (HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice, CV-1 cell line, cell strains derived from in vitro culture of primary tissue or primary explants).

It is contemplated that plasma derived transferrin is isolated from a suitable fraction of plasma. In a preferred embodiment transferrin is isolated from fraction IV, and most preferably fraction IV-I or fraction IV-IV, of the Cohn fractionation process. In another preferred embodiment, transferrin derives from a waste fraction of a method of purifying alpha$_1$-proteinase inhibitor (A1PI). Preferably said purifying method is as follows:
 (a) removing a portion of contaminating proteins from the aqueous solution by precipitation in order to obtain a purified solution containing A1PI;
 (b) passing the purified solution through an anion exchange resin so that A1PI binds to the anion exchange resin;
 (c) eluting A1PI from the anion exchange resin to obtain an eluted solution containing A1PI;
 (d) passing the eluted solution through a cation exchange resin;
 (e) collecting a flow-through from the cation exchange resin that contains A1PI; and
 (f) contacting the eluted solution of step (c) or the flow-through of step (e) with a hydrophobic adsorbent of at least one HIC medium.

In the most preferred embodiment, the aqueous solution used in the method of purifying (A1PI) mentioned above is blood, plasma or a plasma derived fraction.

In a further embodiment transferrin comprises at least one post translational modification, preferably pegylation, glycosylation, polysialylation or combination thereof.

In one embodiment, transferrin used in the method of treatment of the present invention is a full length transferrin with the amino acid sequence set forth in SEQ ID NO: 1. Further embodiments encompass the use in the method of treatment of the present invention of transferrin derivatives with at least 50%, 60%, 70%, 80%, 90%, 95%, 96%, 97%, 98% or 99% homology or similarity with SEQ ID NO: 1 as long as 70%, 80%, 90%, 95%, 96%, 97%, 98%, 99% or 100% of the iron chelating activity of the wild-type transferrin is preserved. A person skilled in the art would readily recognize that the differences in homology between transferrin and the amino acid sequence SEQ ID NO: 1 can be due to conservative and/or non-conservative amino acid substitutions that do not affect the iron chelating function.

In another embodiment, it is contemplated that a fragment of the wild-type transferrin (SEQ ID NO: 1) is used in the method of treatment of the present invention. A person skilled in the art would readily select a suitable fragment of the wild-type transferrin so that it keeps the iron chelating activity of the wild-type transferrin.

In an additional embodiment, transferrin is modified to increase its iron binding affinity. A person skilled in the art would envisage that the residues or zones to be modified can be determined by several techniques know in the art as, for example, site directed mutagenesis, alanine screening, crystallography or analysis of deletions and/or insertions.

It is contemplated that transferrin used in the method of treatment of the present invention is in the form of a protein conjugate or a fusion protein in order to, for example, extend its half-life in blood, wherein transferrin is conjugated or fused to any other protein, protein fragment, protein domain or peptide. In a preferred embodiment, transferrin is conjugated or fused to a full-length, fragment, domain or peptide of serum albumins (as for example, bovine, from rabbits or from humans), keyhole limpet hemocyanin, immunoglobulin molecules (including Fc domain of immunoglobulins), thyroglobulin, ovalbumin, tetanus toxoid, or a toxoid from other pathogenic bacteria, such as diphtheria, *E. coli*, cholera, or *H. pylori*, or an attenuated toxin derivative, cytokines, chemokines, glucagon-like peptide-1, exendin-4 or XTEN.

The transferrin used in the method of the present invention can be Holo-Tf alone, Apo-Tf alone, or a mixture of ApoTf and HoloTf. In a preferred embodiment, the transferrin used in the method of the present invention is a mixture of ApoTf and HoloTf and, preferably, said mixture has a percentage ratio between 99:1 and 70:30 (ApoTf: HoloTf), even more preferably, said mixture has a proportion or percentage ratio that is comparable to that of a fraction obtained or purified from biological fluids. In the most preferred embodiment the mixture of ApoTf and HoloTf used in the method of the present invention has a proportion or percentage ratio of ApoTf and HoloTf as the proportion or percentage ratio of ApoTf and HoloTf present in human blood or plasma.

In the method of the present invention, the composition can further comprise an iron chelator. In a preferred embodiment, the iron chelator is selected from the group comprising M30, deferoxamine (DFO), deferasirox, deferiprone, deferitrin, L1NAll, CP363, CP502, IOX2 ethylenediaminetetraacetic acid (EDTA) or combinations thereof. In the most preferred embodiment, the iron chelator is deferoxamine (DFO).

In the method of the present invention, treatment of Hypoxia Inducible Factor (HIF)-related condition comprises treatment of organs with a composition comprising transferrin in preparation for transplantation into a human. In a preferred embodiment, organs are selected from the group comprising kidney, liver, lung, and heart.

Moreover, in the method of the present invention, treatment of Hypoxia Inducible Factor (HIF)-related condition comprises administration of a composition comprising transferrin to organ transplant recipients prior to or after the transplantation. In a preferred embodiment, the method of the present invention comprises administration of a composition comprising transferrin to organ transplant recipients prior to or after the transplantation, and where transplant organs have been previously treated with a composition comprising transferrin in preparation for transplantation into a human.

In another aspect, the present invention refers to a method of treatment of Hypoxia Inducible Factor (HIF)-related condition, wherein said condition comprises treatment of ischemia in a human comprising the administration to said human of a composition comprising transferrin. In a preferred embodiment, said ischemia is due to cardiac arrest, thrombotic clots, traumatic injury or stroke.

In yet another aspect, the present invention refers to a method of treatment of Hypoxia Inducible Factor (HIF)-related condition, wherein said treatment is a pre-surgical administration to a human patient in cases when ischemia or oxygen deprivation of tissues/organs is observed or anticipated.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Experiments performed in the following examples were treated with transferrin comprising either the Apo- or Holo-forms. A broad variety of transferrin mixtures were tested; the relative percentages of ApoTf and HoloTf comprising majority ApoTf, majority HoloTf, pdTf and specifically defined transferrin mixtures are highlighted in Table 1 below.

TABLE 1

|  | Majority Apo | Majority Holo | Mix 1 | Mix 2 | Mix 3 | pdTf |
|---|---|---|---|---|---|---|
| % ApoTf | 98 | 30 | 95 | 64 | 33 | 68 |
| % HoloTf | 2 | 70 | 5 | 36 | 67 | 32 |

Example 1

Compositions Comprising Majority ApoTf and Majority HoloTf Induce HIF1alpha Protein Under Normoxic and Hypoxic Conditions after 6 Hours of Treatment Human neuroblastoma SH-SY5Y cell line cells, cultured in serum free media were treated with plasma derived ApoTf and HoloTf (in both cases at a concentration of 1 mg/mL and 4 mg/mL) for 6 hours under normoxia (21% oxygen) and hypoxia conditions (1% oxygen). As controls, untreated cells or cells treated with human serum albumin (HSA) at a concentration of 1 mg/mL or 4 mg/mL, are used. After 6 hrs intracellular proteins were harvested and tested for HIF1alpha protein levels by ELISA.

As shown in FIG. 1, a significant increase in HIF-1α cellular protein levels occurred under both normoxic and hypoxic conditions and for the two concentrations tested for ApoTf. Regarding HoloTf a significant increase in the cellular protein levels of HIF-1α was observed for both normoxic and hypoxic conditions when cells were treated with the 1 mg/mL concentration and for normoxic condition when cells were treated with the 4 mg/mL concentration. When cells were treated with the 4 mg/mL concentration of HoloTf a tendency towards an increase in the cellular protein levels of HIF-1α was seen.

Example 2

Figure 2:
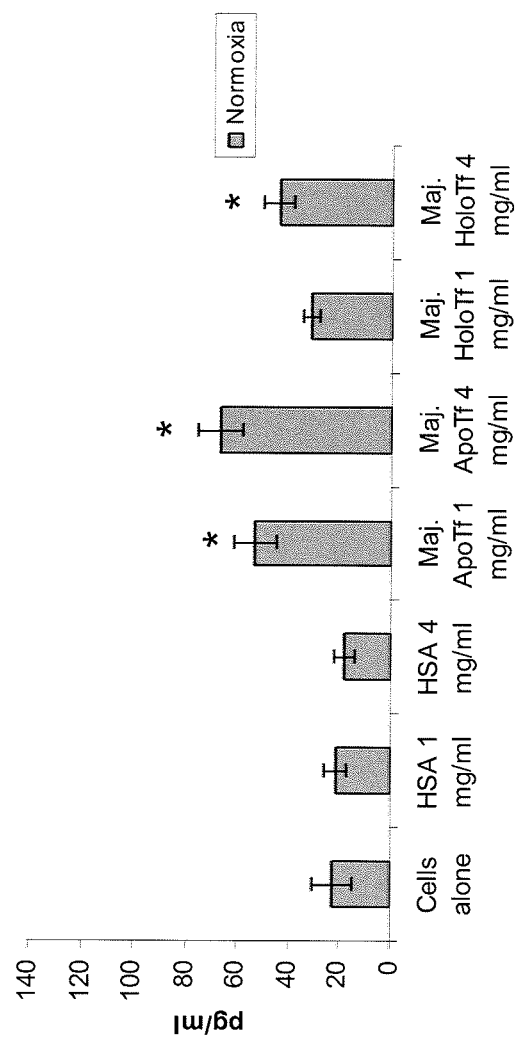
FIG. 2 shows that compositions of majority ApoTf and majority HoloTf induce HIF1alpha protein under normoxic conditions 24 hrs post treatment.

Compositions Comprising Majority ApoTf and Majority HoloTf Induce HIF1alpha Protein Under Normoxic Conditions after 24 Hours of Treatment Experiment performed in example 1 was repeated but performing treatments for 24 hours and only under normoxic conditions. After 24 hrs intracellular proteins were harvested and tested for HIF1 alpha protein levels by ELISA. FIG. 2 shows the results obtained for this experiment. As can be seen in said figure, ApoTf increased cellular protein levels of HIF-1α in both concentrations tested. For HoloTf a significant increase of cellular protein levels of HIF-1α was observed when treatment was performed using a concentration of 4 mg/mL and a tendency towards an increase of said protein was seen when using the 1 mg/mL concentration.

Example 3

Figure 3:
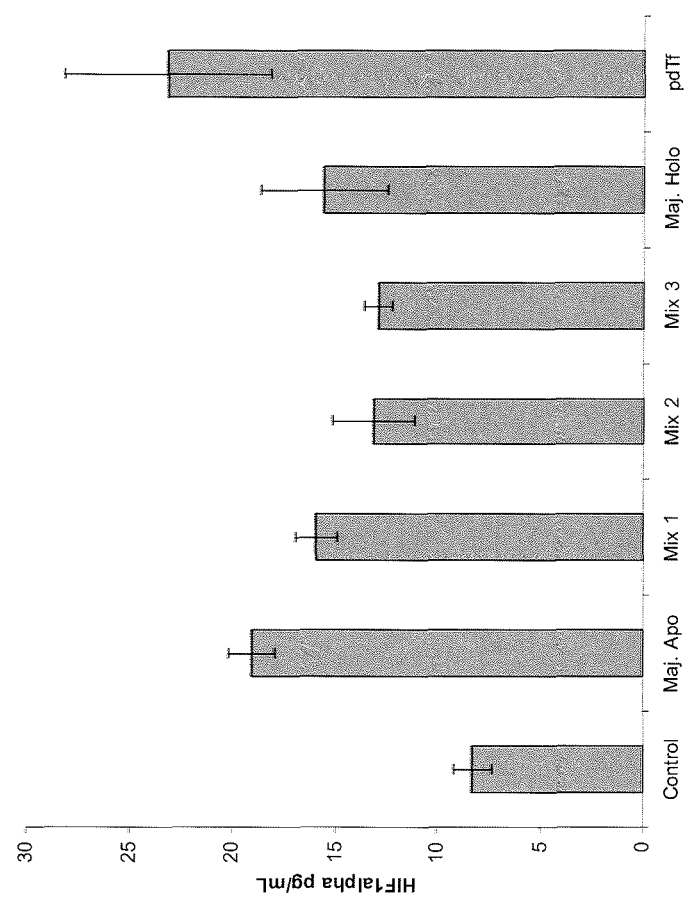
FIG. 3 shows that mixtures of ApoTf and HoloTf induce HIF1 alpha protein 6 hrs post treatment.

Mixtures of ApoTf and HoloTf Induce HIF1 Alpha Protein after 6 Hours of Treatment After 6 hrs, intracellular proteins were harvested and tested for HIF1 alpha protein levels by ELISA. As shown in FIG. 3, an increase of HIF-1a cellular protein levels after 6 hours treatment with plasma derived majority ApoTf, majority HoloTf or mixtures thereof under normoxic conditions was observed. As also can be seen in said figure, all mixtures of ApoTf and HoloTf upregulate HIF1alpha protein in SH-SY5Y neuronal cells.

Figure 4A:
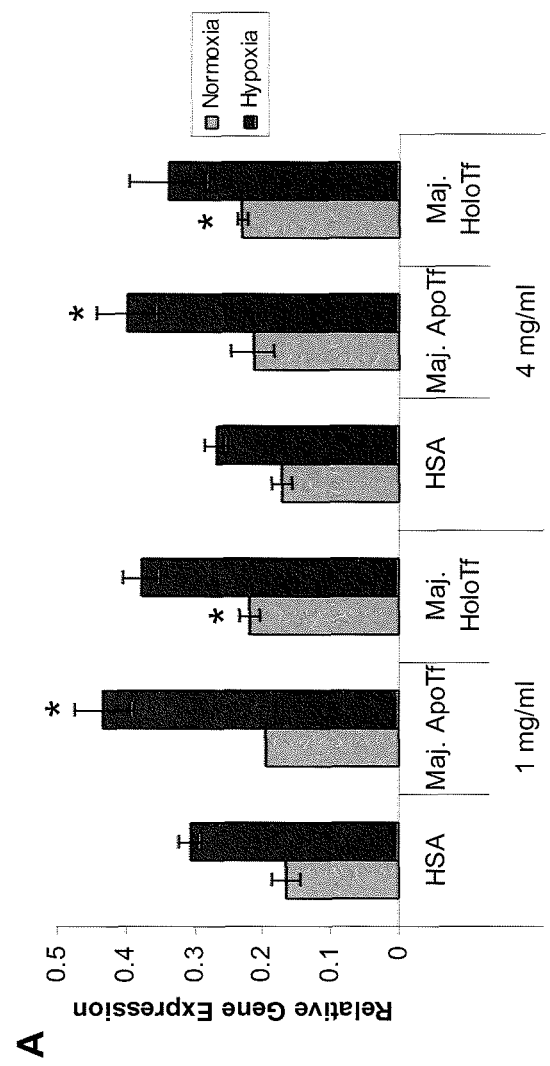
FIG. 4A shows mRNA expression levels of Glut1 under normoxic and hypoxic conditions in the presence of HSA, Apo-transferrin or Holo-transferrin.
Figure 4B:
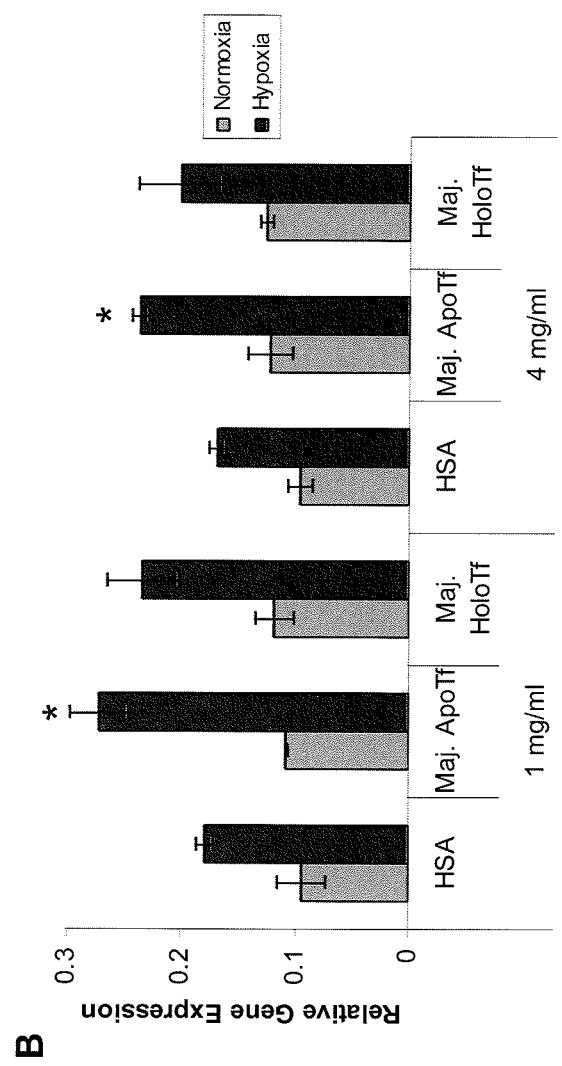
FIG. 4B shows mRNA expression levels of VEGF under normoxic and hypoxic conditions in the presence of HSA, Apo-transferrin or Holo-transferrin.

Example 4 mRNA Expression Levels of Glut1 and VEGF Under Normoxic and Hypoxic Conditions in the Presence of HSA, Apo-Transferrin or Holo-Transferrin The stabilization of, and increase in, HIF-1α protein typically leads to an up-regulation of HIF-related genes (increase in the transcription of genes targeted by HIF), i.e. genes that have HIF binding sites in their transcriptional regulatory elements. Two well characterized genes that are activated by HIF-1α protein are Glut1 receptor and VEGF. Therefore, in order to analyze mRNA expression changes in each of these HIF target genes SH-SY5Y cell line cells were cultured and treated with majority ApoTf or majority HoloTf at a concentration of 1 mg/mL and 4 mg/mL under normoxic (21% oxygen) or hypoxic (1% oxygen) conditions for 6 hours. As a negative controls, cells were treated with HSA (1 mg/mL or 4 mg/mL) or were left untreated. After 6 hrs, intracellular mRNA was harvested and tested for Glut1 and VEGF expression levels by qPCR. Expression results were calculated relative to the expression of the corresponding transcript seen in untreated cells. FIGS. 4A and 4B show the expression results obtained for Glut1 receptor and VEGF, respectively. Values in the figures are shown as Relative Gene Expression, with the target gene (Glut1 or VEGF) normalized for housekeeper (beta-actin) expression. As can be directly derived from said figures, under hypoxic conditions, expression of both Glut1 (FIG. 4A) and VEGF (FIG. 4B) were significantly increased when treated with Apo-transferrin relative to HSA controls. Interestingly, under normoxic conditions, Holo-transferrin, but not Apo-transferrin, increased expression of only Glut1.

Example 5

Mixtures of ApoTf and HoloTf do not Show Toxicity In Vitro or In Vivo

Figure 5A:
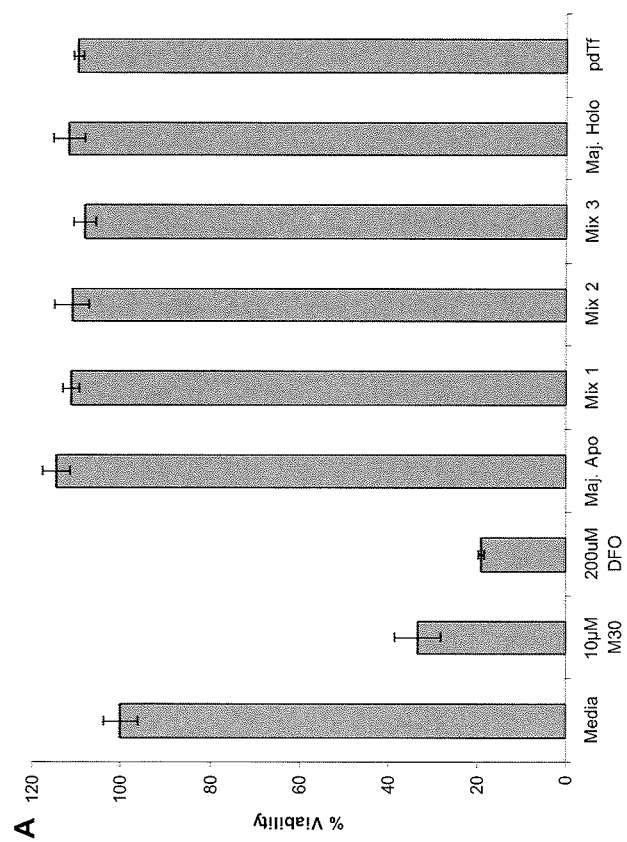
FIG. 5A shows in vitro or in vivo toxicity of compositions comprising either majority HoloTf or majority ApoTf.

Since it has been reported that HoloTf is toxic to cells in vivo and in vitro, toxicity of various compositions containing majority ApoTf, majority HoloTf or mixtures of ApoTf+HoloTf was tested in SH-SY5Y cells. SH-SY5Y cells were treated with the indicated concentrations of 4 mg/mL Tf (as indicated in FIG. 5A), M30 or DFO for 72 hours. After 72 hours, cells were subjected to a Cell Titer Glow viability assay. Control cells, untreated cells, were set to a value of 100% viable. The average viability and standard deviations are shown for each treatment condition. No toxic effects were seen with any composition containing majority ApoTf and, surprisingly, no toxicity or detrimental effects of majority HoloTf were observed.

Interestingly, neither compositions of majority ApoTf nor majority HoloTf showed significant differences in these behavioral criteria, suggesting that there were no detrimental effects of HoloTf in vivo. FIG. 5B shows modified Bederson and General Behavioral scores for rats intravenously treated with drug comprising majority of ApoTf or HoloTf. In vivo neurological function was assessed by a modified Bederson score (Bederson et al., 1986b; Crumrine et al., 2011) using the following definitions:

Score 0: No apparent neurological deficits;
Score 1: Body torsion present;
Score 2: Body torsion with right side weakness;
Score 3: Body torsion, right side weakness with circling behavior; and
Score 4: Seizure Activity.

General behavioral scores of rats were developed by the CALS personnel for the purpose of monitoring recovery of animals following surgical procedures (standard CALS post-operative care). A numerical value was assigned to the predetermined behavioral observations.

Score 0: Behavior consistent with a normal naïve rat (i.e. no ipsilateral deficit);
Score 1: Bright/active/responsive; the rat spontaneously moves and explores his cage, responds to external stimuli, explores the top of the cage;
Score 2: Quiet/alert/responsive; reserved behavior but will respond to external stimulus, tends not to rear or explore the top of the cage;
Score 3: Depressed behavior: tends not to move unless prodded, quickly returns to a somnolent state, little to no interest in external stimuli;
Score 4: Unresponsive: remains in a prostrate position even when prodded; and Score 5: Seizure activity requiring euthanasia.

Example 6

In Vivo Cellular Protection by Transferrin

Figure 6A:
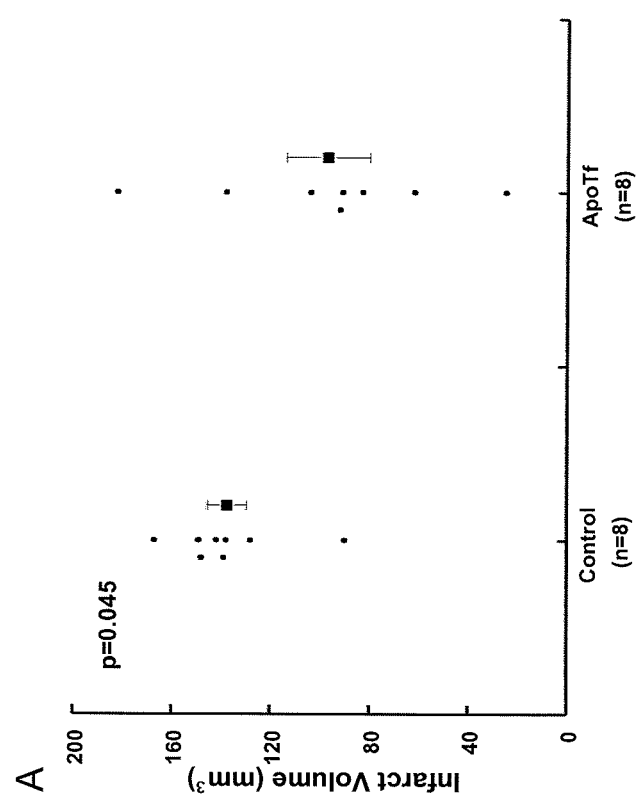
FIG. 6A shows Scatter plot of the infarct volume of ApoTf (385 mg/kg, IV) or saline treatment in transient Middle Cerebral Artery occlusion (MCAo) rat model.
Figure 6B:
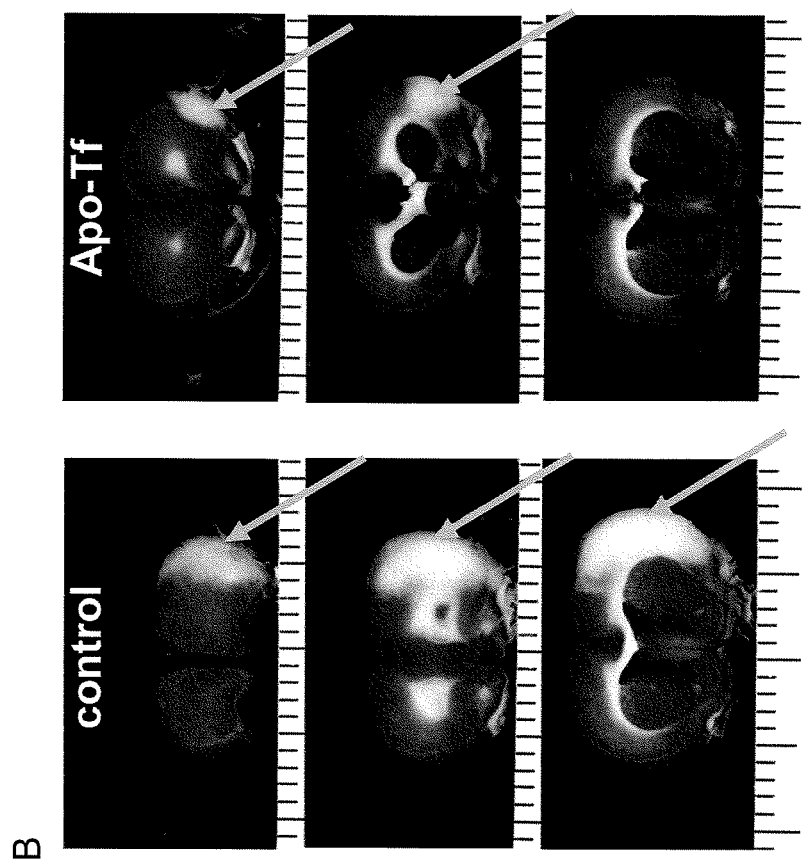
FIG. 6B shows triphenyltetrazolium chloride (ITC) stained Coronal sections from a representative control and ApoTf treated rat.

The MCAo (Middle Cerebral Artery occlusion) rat model of brain stroke was used to assess cellular protection by transferrin. Stroke was surgically induced to 16 rats by using the MCAO technique. 8 rats were treated by injection of saline solution in the brain and the other 8 by injection of ApoTf in the brain. FIGS. 6A and 6B show that a significant decrease in the volume of the infracted area was observed in the rats treated with a mixture comprising a majority of ApoTf when compared with control rats (treated with saline solution). FIG. 6A shows a scatter plot of the infarct volume of ApoTf (385 mg/kg, IV) or saline treatment in transient MCAo; and FIG. 6B shows TTC stained Coronal sections from a representative control and ApoTf treated rat.

Example 7

ApoTf and HoloTf Protect SH-SY5Y from Abeta 1-42 Toxicity

Figure 7:
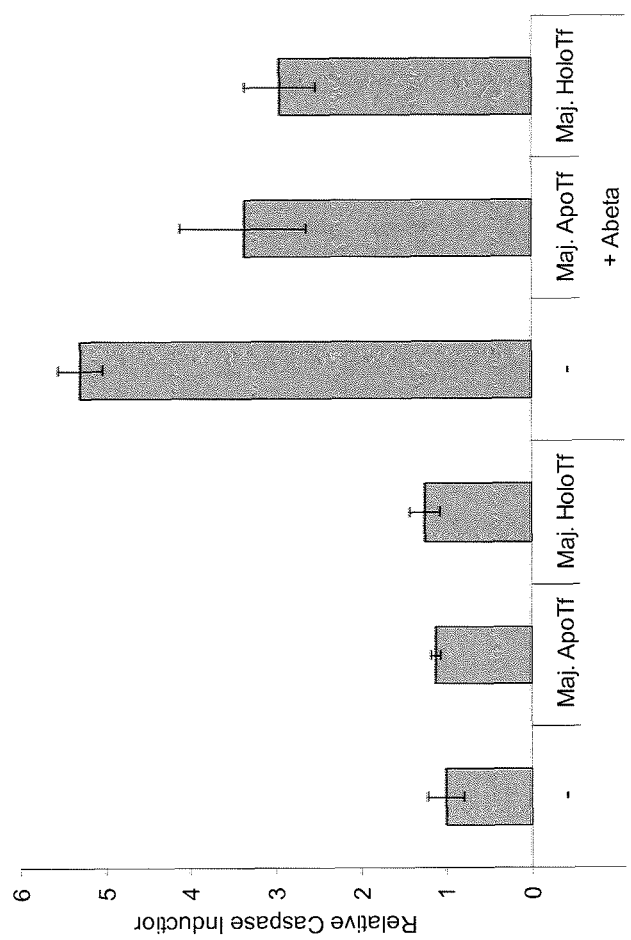
FIG. 7 shows protection of neuronal cells from the toxic effects of Abeta(1-42) by mixtures comprising mostly ApoTf and HoloTf.

Upregulation of the HIF pathway is known to play a protective role in a number of neurodegenerative diseases, including pathologies that result in destruction of nerve cells and neurons. Since treatment of SH-SY5Y upregulates HIF, treatment of cells with Apo- or Holo-transferrin should provide a protective effect on cells subjected to substances known to induce neurodegeneration. FIG. 7 highlights data assessing whether majorities of Apo- and Holo-transferrin could protect SH-SY5Y cells from the toxic effects of the known neurodegenerative toxin oligomerized Abeta 1-42 peptide (FIG. 7). SH-SY5Y neuronal cells cultured in growth media were treated with 4 mg/mL Apo-transferrin or Holo-transferrin for 24 hrs under normal oxygen levels. After 24 hrs, cells were treated with oligomerized Abeta1-42 peptide for an additional 72 hours. Following treatment with oligomerized Abeta1-42, cells were subjected to a ApoGlo caspase 3/7 activation assay. Control cells, untreated cells, were set to a normalized value of 1. The average caspase induction, relative to control cells, and standard deviations are shown for each treatment condition. Interestingly, these data show that both majority ApoTf and HoloTf protect SH-SY5Y cells from Abeta induced toxicity. These data also further confirm lack of inherent toxicity with either ApoTf or HoloTf.

Example 8

Synergystic Effect with Small Molecule HIF Activators and ApoTf/HoloTf Mixtures

Figure 8A:
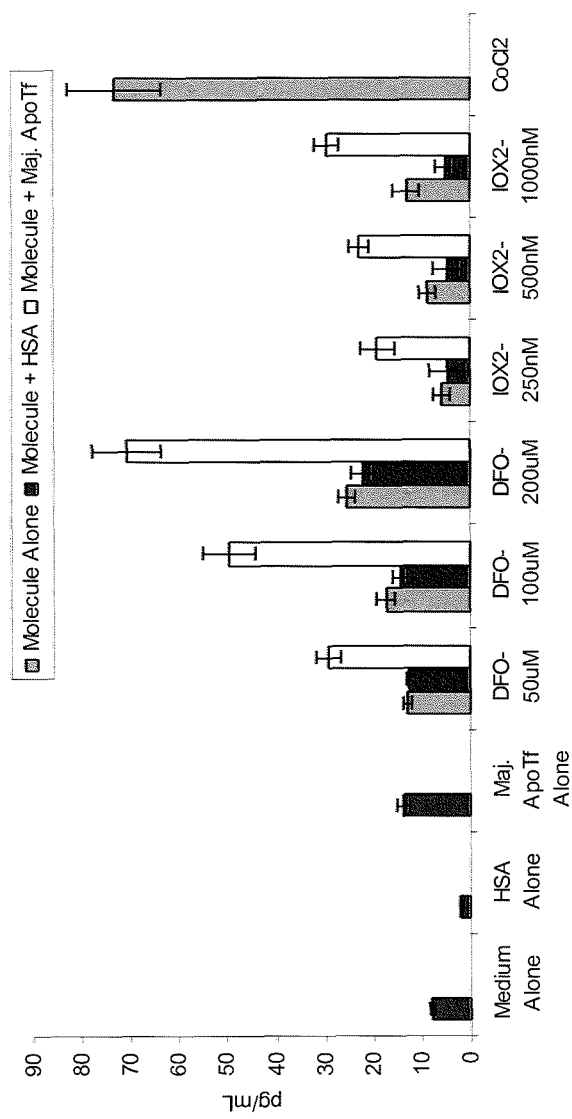
FIG. 8A shows treatment of SH-SY5Y neuronal cells with 4 mg/ml of majority ApoTf and with a combination of majority ApoTf and DFO or IOX2.
Figures 8B, 8C:
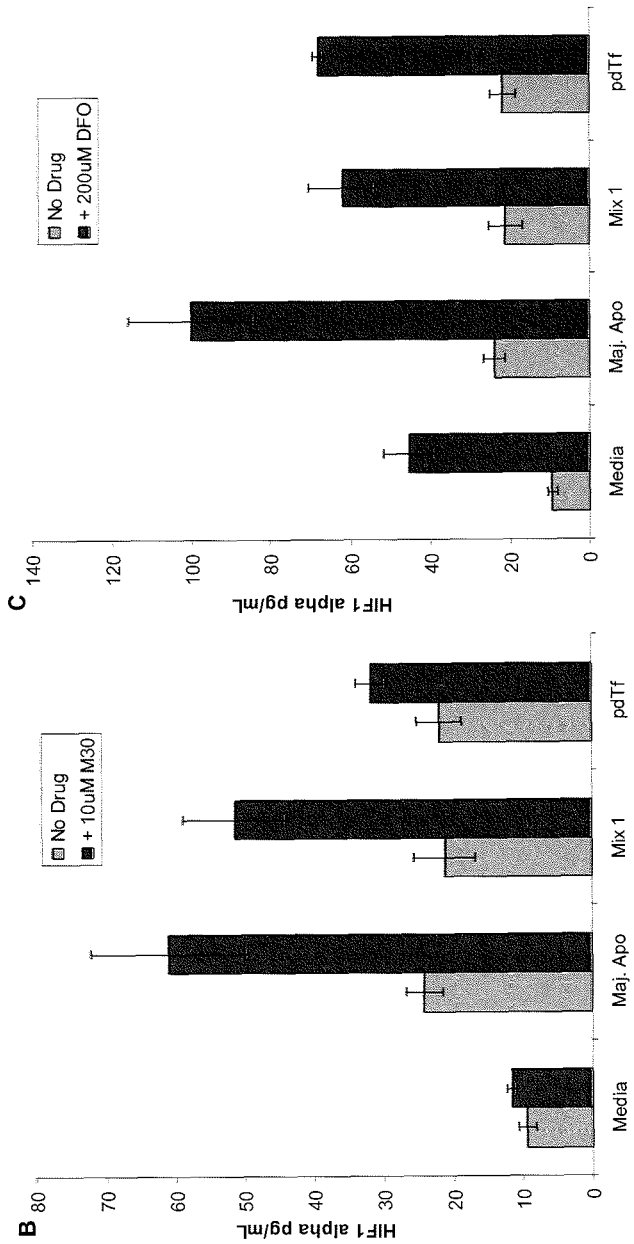
FIG. 8B shows treatment of SH-SY5Y neuronal cells with 4 mg/ml of the indicated protein and with a combination of the indicated protein and 10 uM M30 plus.
FIG. 8C shows treatment of SH-SY5Y neuronal cells with 4 mg/ml of the indicated protein and with a combination of the indicated protein and 200 uM DFO.

Transferrin may act synergistically with other HIF activating small molecules, such as other iron chelators or enzyme inhibitors. This could allow lower levels of these small molecules to be administered, eliciting fewer side effects but retaining high therapeutic levels. To determine whether Apotransferrin increases the potency of the iron chelator, DFO, and the phd2 inhibitor IOX2; SH-SY5Y neuronal cells cultured in serum free media were treated with 4 mg/mL of the indicated proteins in the presence or absence of small molecule drug under normal oxygen levels. The results of the experiment are shown in FIGS. 8A, 8B, and 8C. The data shown in FIG. 8A relates to treatment of cells with a combination of DFO or IOX2, at the indicated concentrations, plus 4 mg/mL protein. $CoCl_2$ was used as an experimental positive control. The data shown in FIG. 8B relates to treatment of cells with a combination of 10 uM M30 plus/minus 4 mg/mL protein. The data shown in FIG. 8C relates to treatment of cells with a combination of 200 uM DFO plus/minus 4 mg/mL protein. After 6 hrs intracellular proteins were harvested and tested for HIF1 alpha protein levels by ELISA. Data are shown in pg/mL with standard deviation.

Figure 9A:
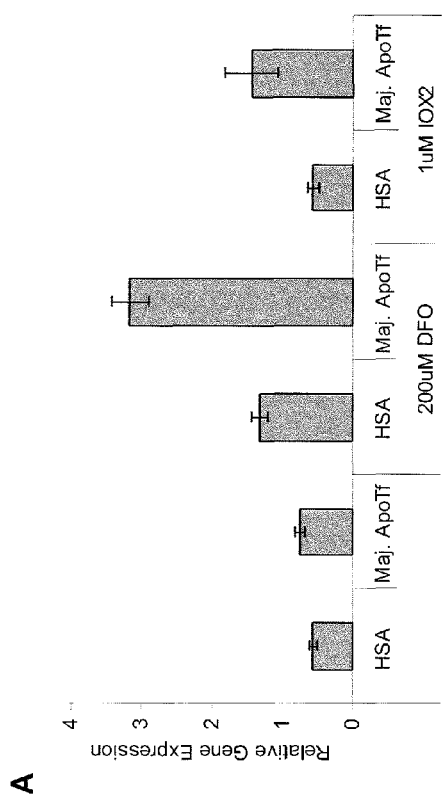
FIG. 9A shows mRNA expression levels of Glut1 in response to majority Apotransferrin and DFO or IOX2 combinations.
Figure 9B:
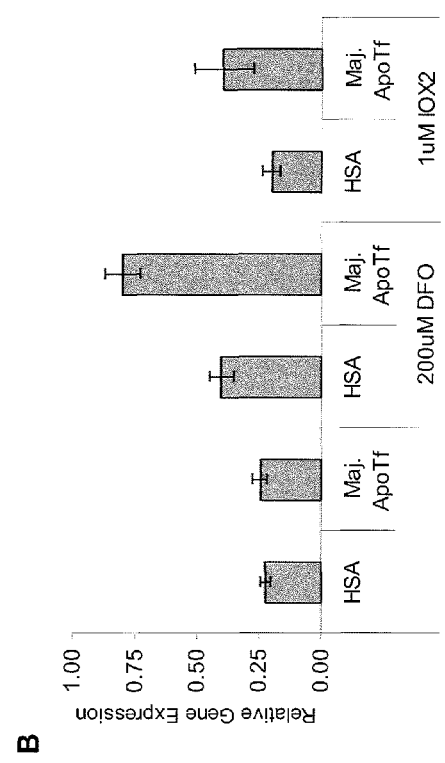
FIG. 9B shows mRNA expression levels of VEGF in response to majority Apotransferrin and DFO or IOX2 combinations.

Example 9 mRNA Expression Levels of Glut1 and VEGF in Response to Majority Apotransferrin and DFO or IOX2 Combinations In addition, mRNA expression levels of Glut1 and VEGF in response to majority Apotransferrin and DFO or IOX2 combinations were determined. SH-SY5Y neuronal cells cultured in serum free media were treated with 4 mg/mL human serum albumin or majority Apotransferrin under normal oxygen levels. Where indicated, either 200 uM DFO or 1 uM IOX2 were co-treated with the HSA and majority Apotransferrin. After 6 hr treatments, intracellular mRNA was harvested and tested for Glut1 and VEGF expression levels by qPCR. Values are shown as Relative Gene Expression, with the target gene (Glut1 or VEGF) normalized for housekeeper (beta-actin) expression. Standard deviations are shown. FIGS. 9A and 9B show that Glut1 and VEGF mRNA levels increase synergistically and additively with the addition of both Apotransferrin and small molecule activators of the HIF pathway.

Example 10

Figure 10A:
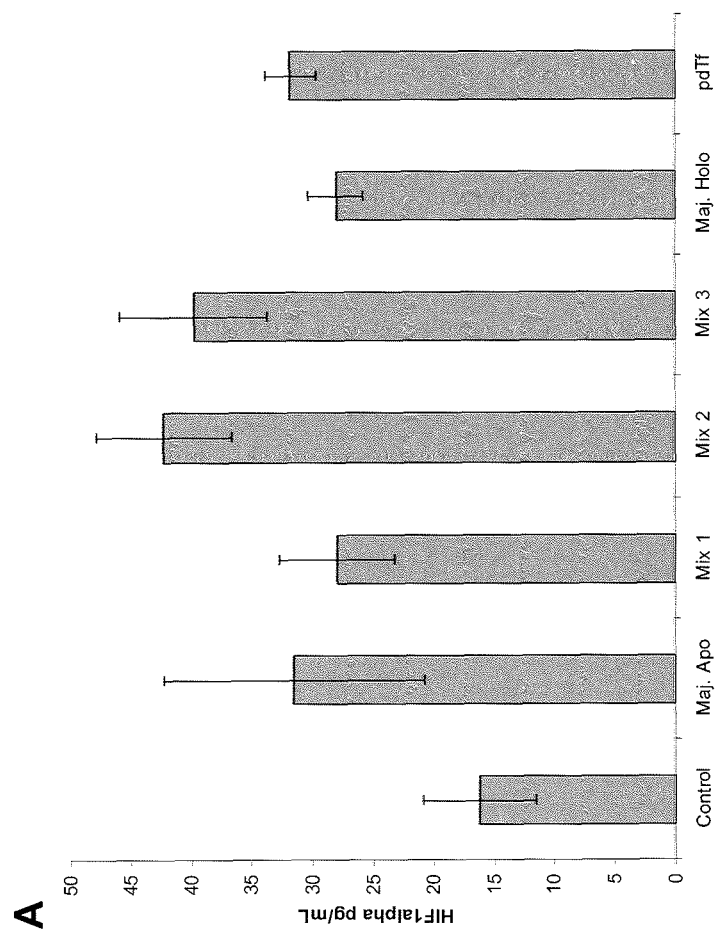
FIG. 10A shows HIF1 alpha levels after treatment of Primary human renal proximal tubule epithelial (RPTEC) cells with 4 mg/mL majority Apo-transferrin, majority Holo-transferrin or various mixtures of each for 6 hrs under normal oxygen levels.
Figure 10B:
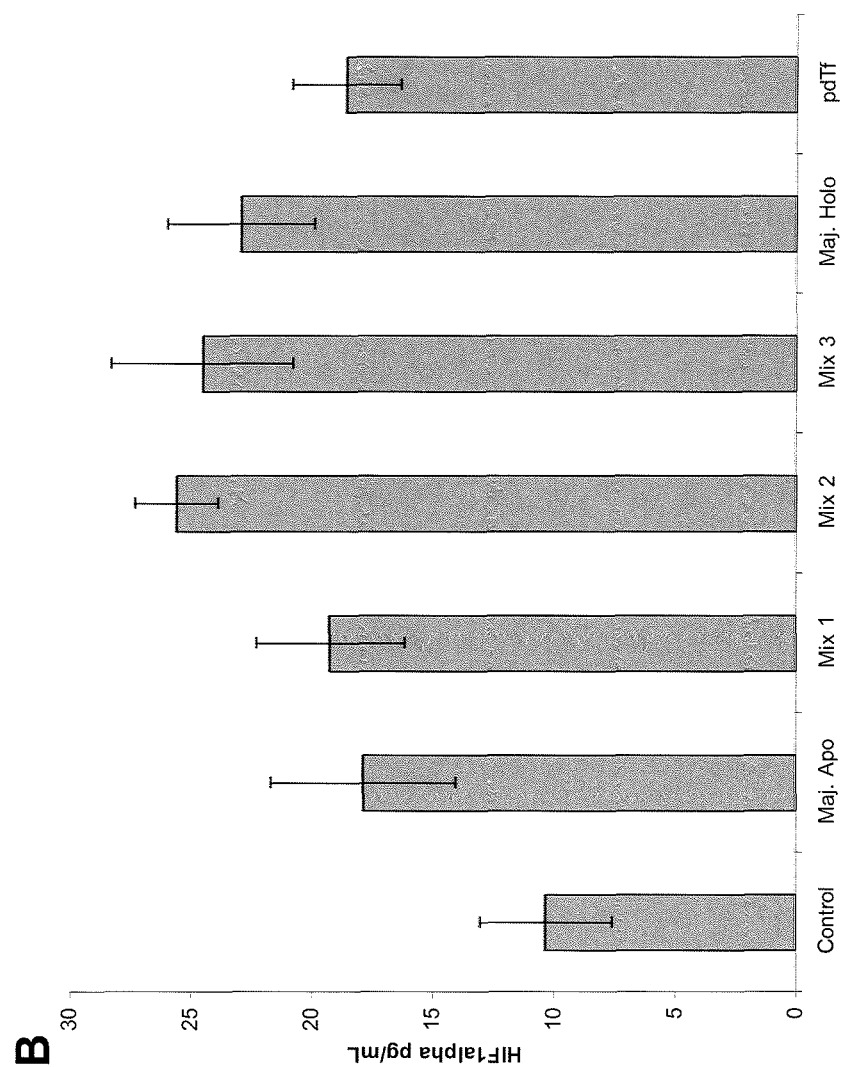
FIG. 10B shows HIF1 alpha levels after treatment of primary cortical epithelial (HRCE) cells with 4 mg/mL majority Apo-transferrin, majority Holo-transferrin or various mixtures of each for 6 hrs under normal oxygen levels.

Compositions of Majority ApoTf and Majority HoloTf Induce HIF1 Alpha Protein in Human Primary Kidney Cells It is well-known in the art that many small molecules used for the treatment of conditions related or provoked by hypoxia are toxic and have numerous side effects, e.g. DFO. One of the most apparent side effects of said small molecules is kidney toxicity. Therefore, in order to assess whether transferrin and/or mixtures increase HIF1 alpha levels in primary kidney cells; human primary kidney cells, both primary human renal proximal tubule epithelial (RPTEC) or cortical epithelial cells (HRCE) were obtained. Primary human renal proximal tubule epithelial (RPTEC) or primary cortical epithelial (HRCE) cells cultured in serum free media were treated with 4 mg/mL majority Apo-transferrin, majority Holo-transferrin or various mixtures of each for 6 hrs under normal oxygen levels. After 6 hrs intracellular proteins were harvested and tested for HIF1 alpha protein levels by ELISA. FIGS. 10A and 10B reveal that HIF1 alpha levels are induced with transferrin composed of mixtures of Apo-transferrin and Holo-transferrin in RPTEC and HRCE, respectively.

Example 11

Figure 11A:
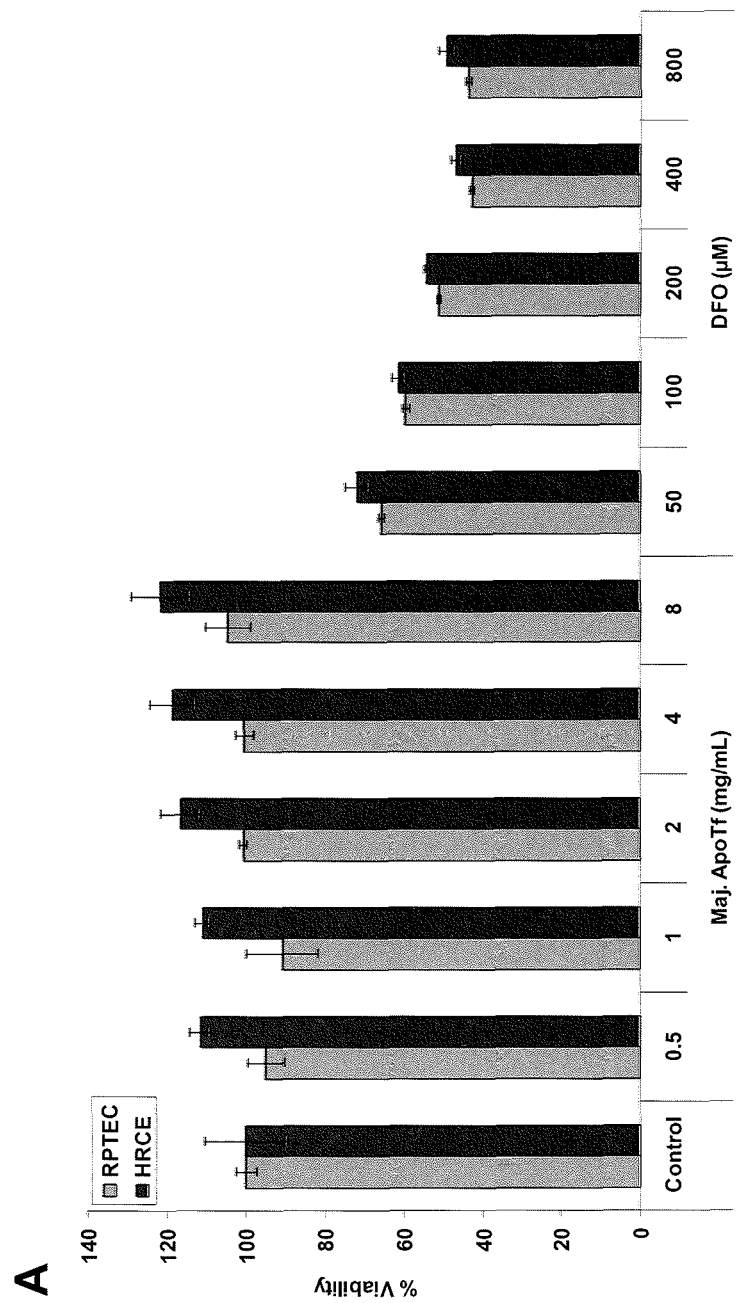
FIG. 11A shows viability of primary human renal proximal tubule epithelial (RPTEC) or cortical epithelial (HRCE) cells when treated with majority ApoTf or DFO for 48 hours.
Figure 11B:
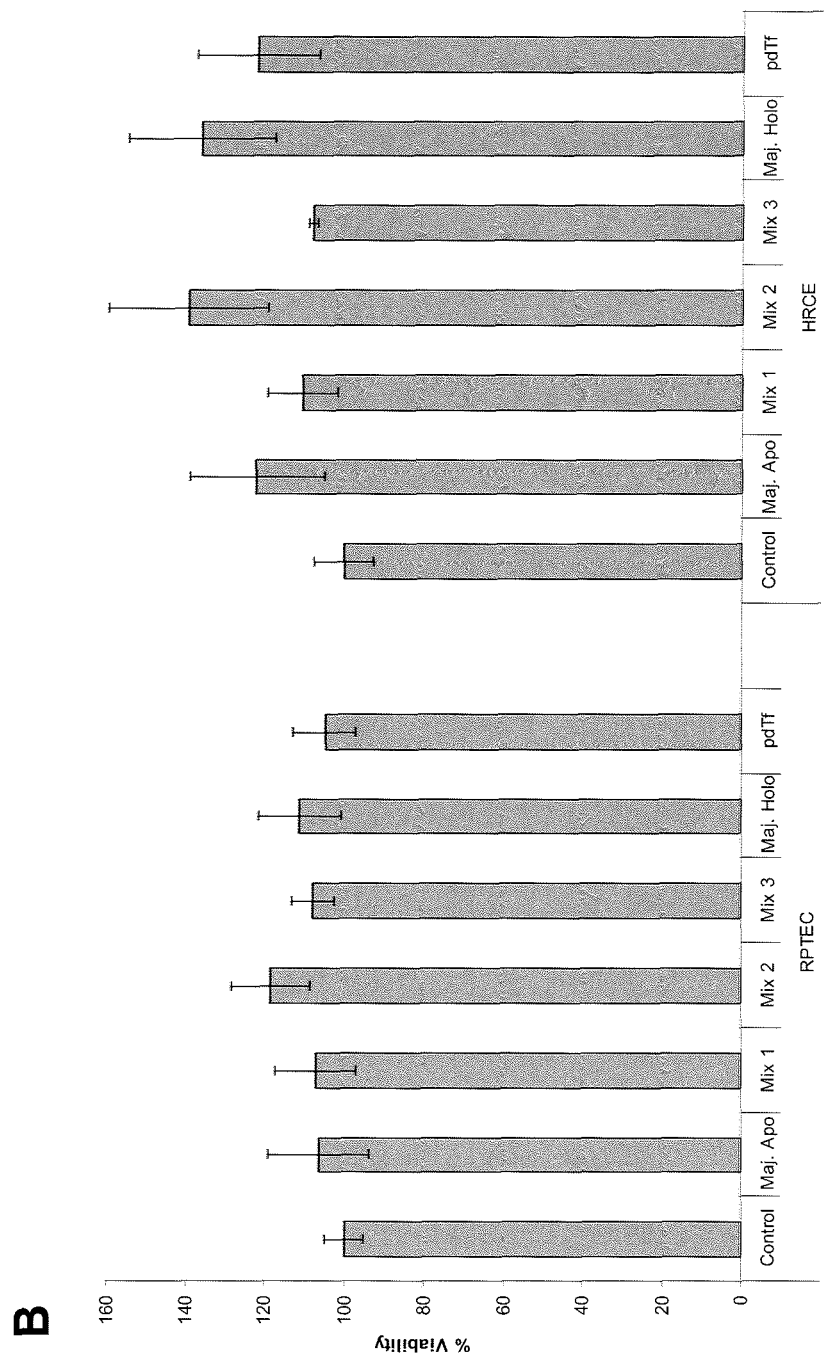
FIG. 11B shows viability of RPTEC or HRCE cells when treated for 72 hrs with 4 mg/mL of majority ApoTf, majority HoloTf, mixtures of transferrin.

Viability of Human Primary Kidney Cells in the Presence of Transferrins or DFO, Including Caspase 3/7 Activation within Human Primary Kidney Cells in the Presence of Majority ApoTf or DFO Considering the anticipated safety profile of a human plasma protein, toxicity of DFO and transferrins (majority Apo, majority Holo and mixtures) was assessed in primary human kidney cells. The renal proximal tubule epithelial (RPTEC) or cortical epithelial (HRCE) cells were treated with the indicated concentrations of majority ApoTf or DFO for 48 hours (FIG. 11A); and RPTEC or HRCE cells were treated for 72 hrs with 4 mg/mL of majority ApoTf, majority HoloTf, mixtures of transferrin (FIG. 11B). After 48 or 72 hours, cells were subjected to a Cell Titer Glow viability assay. Control cells, untreated cells, were set to a value of 100% viable. The average viability and standard deviations are shown for each treatment condition. FIGS. 11A and 11B show that while DFO had significant toxicity, none of the transferrin molecules showed any detrimental effects on these primary kidney cells.

Figure 12:
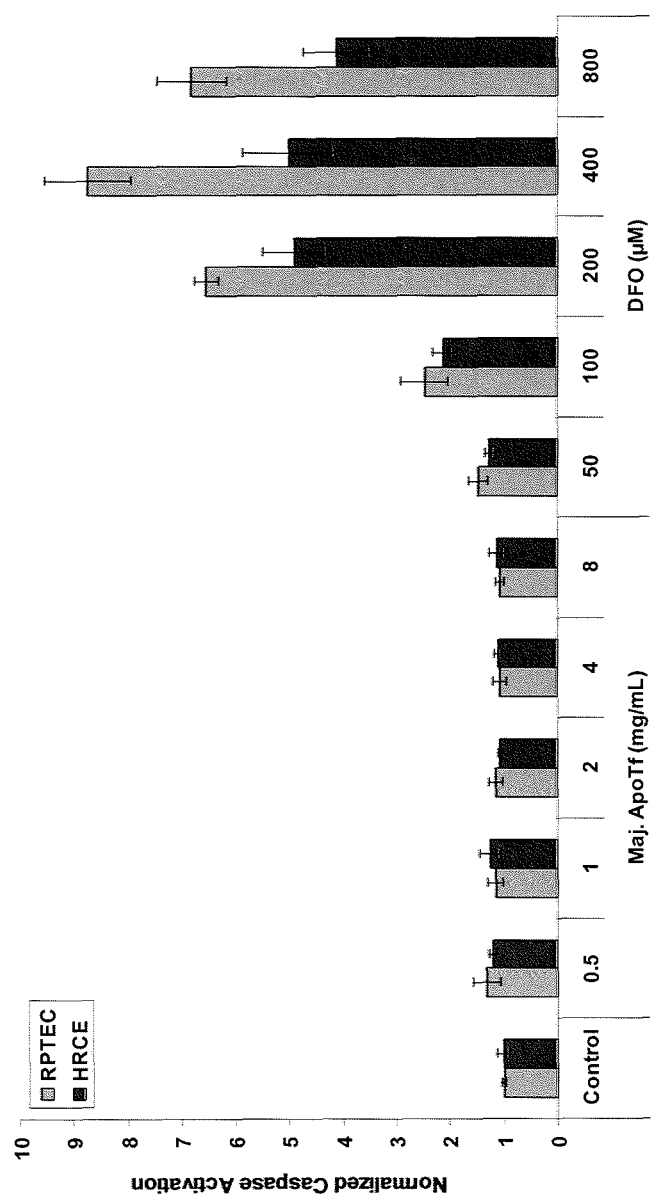
FIG. 12 shows caspase 3/7 activation within human primary kidney cells in the presence of majority ApoTf or DFO.

In order to assess caspase 3/7 activation within human primary kidney cells in the presence of ApoTf or DFO; RPTE or HRC cells were treated with the indicated concentrations of ApoTf or DFO for 48 hours. After 48 hours, cells were subjected to a ApoGlo caspase 3/7 activation assay. Control cells, untreated cells, were set to a normalized value of 1. The average caspase activity, relative to control cells, and standard deviations are shown in FIG. 12 for each treatment condition.

Example 12

Figure 13A:
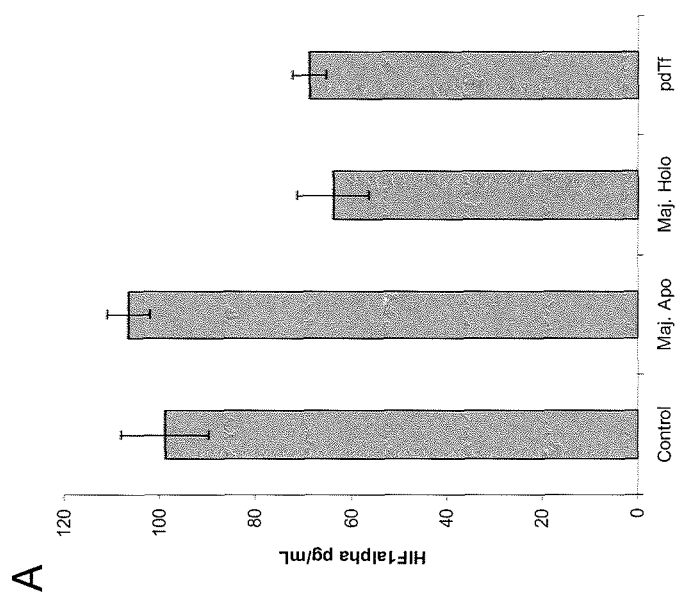
FIG. 13A shows HIF1alpha levels after treatment of lung cell line NCI-H1650 with 4 mg/mL majority Apo-transferrin, majority Holo-transferrin or pd-Transferrin for 6 hrs under normal oxygen levels.
Figure 13B:
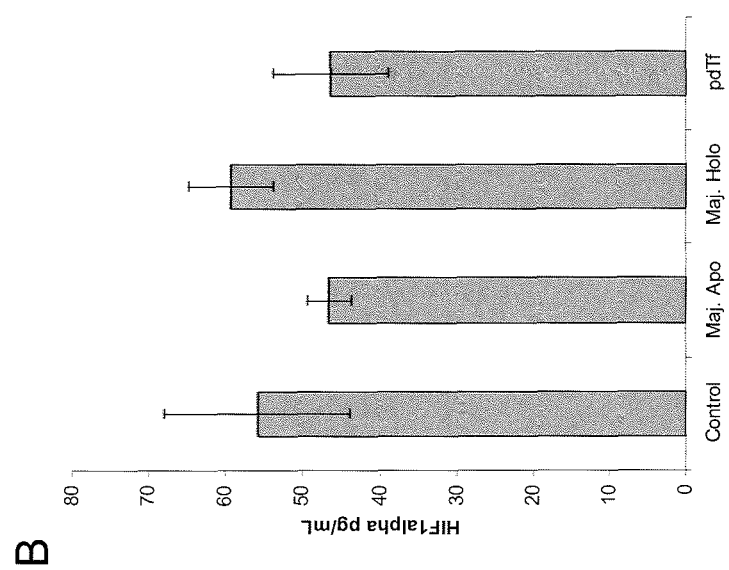
FIG. 13B shows HIF1 alpha levels after treatment of primary hepatocyte cells with 4 mg/mL majority Apo-transferrin, majority Holo-transferrin or pd-Transferrin for 6 hrs under normal oxygen levels.

No Upregulation of HIF was Observed in Primary Human Hepatocytes or NCI-H1650, a Lung Cell Line As detailed above, both plasma derived Apo-transferrin and Holo-transferrin increase the cellular levels of HIF-1alpha, in the human neuronal cell line SH-SY5Y. In addition to neuronal cells, liver and lung organ transplants may also benefit from induction of HIF signaling. Hence, in order to assess the same; effect of transferrins on HIF1alpha levels in primary hepatocytes and a lung cell line (NCI-H1650) was determined. The lung cell line NCI-H1650 or primary hepatocyte cells cultured in serum free media were treated with 4 mg/mL majority Apo-transferrin, majority Holo-transferrin or pd-Transferrin for 6 hrs under normal oxygen levels. After 6 hrs intracellular proteins were harvested and tested for HIF1alpha protein levels by ELISA. The data, as highlighted in FIGS. 13A and 13B, shows that HIF1 alpha levels are not induced with transferrin or mixtures of Apo-transferrin and Holo-transferrin in NCI-H1650 or primary hepatocytes.

Example 13

Figure 14A:
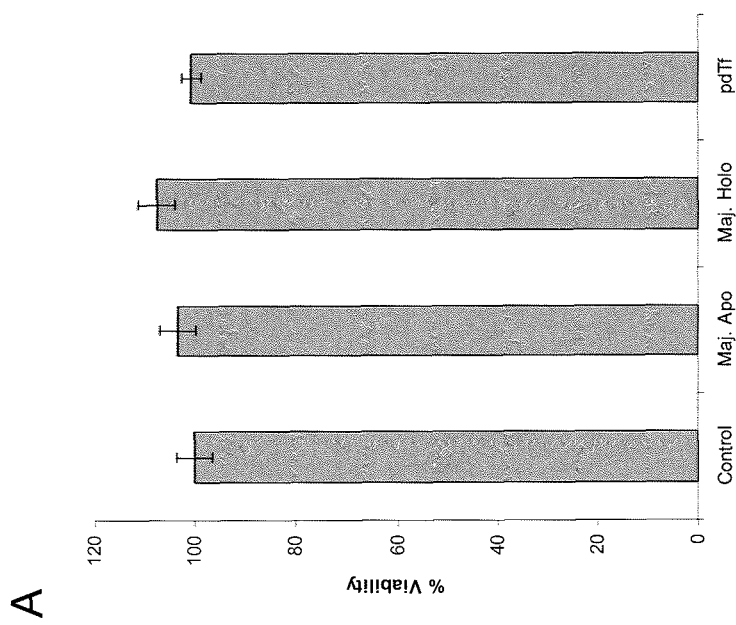
FIG. 14A shows viability of human lung cell line, NCI-H1650, when treated for 72 hours with 4 mg/mL of majority ApoTf, majority HoloTf, or pd-transferrin.
Figure 14B:
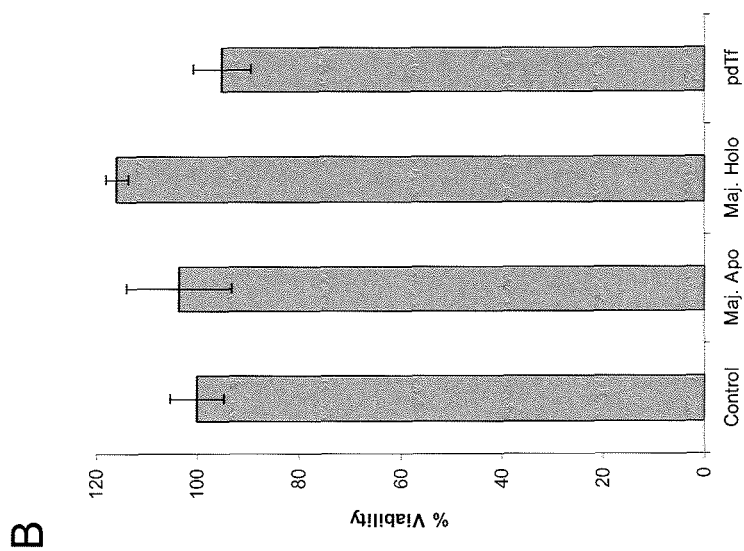
FIG. 14B shows viability of primary human hepatocytes when treated for 72 hours with 4 mg/mL of majority ApoTf, majority HoloTf, or pd-transferrin.

Viability of NCI-H1650 and Human Primary Hepatocytes in the Presence of Transferrins Given the anticipated safety profile of a human plasma protein, toxicity of transferrins (majority Apo, majority Holo and pd-transferrin) in NCI-H1650 and primary human hepatocyte cells was assessed. The human lung cell line, NCI-H1650, and primary human hepatocytes were treated for 72 hours with 4 mg/mL of majority ApoTf, majority HoloTf, or pd-transferrin. After 72 hours, cells were subjected to a Cell Titer Glow viability assay. Control cells, untreated cells, were set to a value of 100% viable. The average viability and standard deviations are shown in FIGS. 14A and 14B for each treatment condition. The data shows that no toxicity was observed with compositions containing either majority HoloTf or majority ApoTf in lung cells, NCI-H1650, or primary hepatocytes.

CONCLUSIONS

The experiments performed in the human neuronal cell line SH-SY5Y showed that both plasma derived Apo-transferrin and Holo-transferrin increased the cellular levels of HIF-1α. The increase in HIF1 alpha levels occurred under both normoxic and hypoxic conditions. Administration of Apo-transferrin to cells under normal oxygen conditions raised the levels of HIF1 alpha to a similar level of that seen when cells were exposed to a hypoxic environment. Exposure of SH-SY5Y cells to Apo-transferrin in normoxic conditions for longer periods increased the level of HIF1 alpha to a greater extent than shorter time. The human serum albumin negative controls had no effect on HIF1-α levels.

Various mixtures of ApoTf and HoloTf all upregulated HIF1 alpha protein in SH-SY5Y neuronal cells and primary kidney cells.

No upregulation of HIF1 alpha was observed in primary human hepatocytes, or NCI-H1650, a lung cell line.

Various mixtures of ApoTf and HoloTf all upregulated HIF1alpha target genes in SH-SY5Y neuronal cells.

No toxicity was observed with compositions containing either majority HoloTf or majority ApoTf in any cell type (neuronal, lung, kidney or hepatocyte) or in vivo.

In vivo treatment of rats in a neurological stress model of ischemia-reperfusion showed that transferrin (composed of mostly ApoTf) protects rat cells from infarct.

Mixtures comprising mostly of ApoTf or HoloTf protected neuronal cells from the toxic effects of Abeta (1-42) oligomer.

Only mixtures composed of majority ApoTf had synergistic effects with M30 or DFO, and these synergistic activities only occurred in SH-SY5Y neuronal cells.

The invention claimed is:

1. A method of treating a Hypoxia Inducible Factor (HIF)-related pathological condition in a patient in need thereof, wherein the HIF-related pathological condition is Middle Cerebral Artery occlusion (MCAo), comprising administering to the patient a composition comprising a therapeutically effective amount of transferrin, and wherein the transferrin is a mixture of apo-transferrin and holo-transferrin in a ratio from 99% Apo-Tf:1% Holo-Tf to 30% Apo-Tf:70% Holo-Tf.

2. The method of claim 1, wherein the composition further comprises an iron chelator or prolyl hydroxylase domain-containing protein 2 (PHD2) enzyme inhibitor.

3. The method of claim 2, wherein the iron chelator is selected from the group consisting of M30, deferoxamine (DFO), Deferasirox, deferiprone, deferitrin, L1NAll, CP363, CP502 and Ethylenediaminetetraacetic acid (EDTA).

4. The method of claim 2, wherein the PHD2 enzyme inhibitor is selected from the group consisting of IOX2, IOX3 and dimethyloxallylglycine.

5. The method of claim 1, wherein the patient is a transplant recipient of an organ.

6. The method of claim 5, wherein the organ has been treated with the composition in preparation for the transplantation into the recipient.

7. The method of claim 6, where the composition further comprises an iron chelator or prolyl hydroxylase domain-containing protein 2 (PHD2) enzyme inhibitor.

8. The method of claim 1, wherein the condition is associated with ischemia or oxygen deprivation in the patient prior to surgery.

9. The method of claim 8, wherein the ischemia is due to cardiac arrest, thrombotic clots, traumatic injury or stroke.

10. The method of claim 1, wherein the condition is associated with interruption of blood flow during a surgical intervention in the patient.

11. The method of claim 1, wherein the transferrin is recombinant.

12. The method of claim 1, wherein the transferrin is modified by pegylation, glycosylation or polysialylation to extend its plasma half-life.

13. The method of claim 1, wherein the composition further comprises an iron chelator.

* * * * *

SEQUENCE LISTING

```
<160> NUMBER OF SEQ ID NOS: 1

<210> SEQ ID NO 1
<211> LENGTH: 698
<212> TYPE: PRT
<213> ORGANISM: Homo sapiens

<400> SEQUENCE: 1

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175
```

-continued

```
Cys Ala Pro Cys Ala Asp Gly Thr Asp Phe Pro Gln Leu Cys Gln Leu
            180                 185                 190
Cys Pro Gly Cys Gly Cys Ser Thr Leu Asn Gln Tyr Phe Gly Tyr Ser
        195                 200                 205
Gly Ala Phe Lys Cys Leu Lys Asp Gly Ala Gly Asp Val Ala Phe Val
    210                 215                 220
Lys His Ser Thr Ile Phe Glu Asn Leu Ala Asn Lys Ala Asp Arg Asp
225                 230                 235                 240
Gln Tyr Glu Leu Leu Cys Leu Asp Asn Thr Arg Lys Pro Val Asp Glu
                245                 250                 255
Tyr Lys Asp Cys His Leu Ala Gln Val Pro Ser His Thr Val Val Ala
            260                 265                 270
Arg Ser Met Gly Gly Lys Glu Asp Leu Ile Trp Glu Leu Leu Asn Gln
        275                 280                 285
Ala Gln Glu His Phe Gly Lys Asp Lys Ser Lys Glu Phe Gln Leu Phe
    290                 295                 300
Ser Ser Pro His Gly Lys Asp Leu Leu Phe Lys Asp Ser Ala His Gly
305                 310                 315                 320
Phe Leu Lys Val Pro Pro Arg Met Asp Ala Lys Met Tyr Leu Gly Tyr
                325                 330                 335
Glu Tyr Val Thr Ala Ile Arg Asn Leu Arg Glu Gly Thr Cys Pro Glu
            340                 345                 350
Ala Pro Thr Asp Glu Cys Lys Pro Val Lys Trp Cys Ala Leu Ser His
        355                 360                 365
His Glu Arg Leu Lys Cys Asp Glu Trp Ser Val Asn Ser Val Gly Lys
    370                 375                 380
Ile Glu Cys Val Ser Ala Glu Thr Thr Glu Asp Cys Ile Ala Lys Ile
385                 390                 395                 400
Met Asn Gly Glu Ala Asp Ala Met Ser Leu Asp Gly Gly Phe Val Tyr
                405                 410                 415
Ile Ala Gly Lys Cys Gly Leu Val Pro Val Leu Ala Glu Asn Tyr Asn
            420                 425                 430
Lys Ser Asp Asn Cys Glu Asp Thr Pro Glu Ala Gly Tyr Phe Ala Val
        435                 440                 445
Ala Val Val Lys Lys Ser Ala Ser Asp Leu Thr Trp Asp Asn Leu Lys
    450                 455                 460
Gly Lys Lys Ser Cys His Thr Ala Val Gly Arg Thr Ala Gly Trp Asn
465                 470                 475                 480
Ile Pro Met Gly Leu Leu Tyr Asn Lys Ile Asn His Cys Arg Phe Asp
                485                 490                 495
Glu Phe Phe Ser Glu Gly Cys Ala Pro Gly Ser Lys Lys Asp Ser Ser
            500                 505                 510
Leu Cys Lys Leu Cys Met Gly Ser Gly Leu Asn Leu Cys Glu Pro Asn
        515                 520                 525
Asn Lys Glu Gly Tyr Tyr Gly Tyr Thr Gly Ala Phe Arg Cys Leu Val
    530                 535                 540
Glu Lys Gly Asp Val Ala Phe Val Lys His Gln Thr Val Pro Gln Asn
545                 550                 555                 560
Thr Gly Gly Lys Asn Pro Asp Pro Trp Ala Lys Asn Leu Asn Glu Lys
                565                 570                 575
Asp Tyr Glu Leu Leu Cys Leu Asp Gly Thr Arg Lys Pro Val Glu Glu
            580                 585                 590
```

```
Tyr Ala Asn Cys His Leu Ala Arg Ala Pro Asn His Ala Val Val Thr
    595             600             605
Arg Lys Asp Lys Glu Ala Cys Val His Lys Ile Leu Arg Gln Gln Gln
    610             615             620
His Leu Phe Gly Ser Asn Val Thr Asp Cys Ser Gly Asn Phe Cys Leu
625             630             635             640
Phe Arg Ser Glu Thr Lys Asp Leu Leu Phe Arg Asp Asp Thr Val Cys
            645             650             655
Leu Ala Lys Leu His Asp Arg Asn Thr Tyr Glu Lys Tyr Leu Gly Glu
            660             665             670
Glu Tyr Val Lys Ala Val Gly Asn Leu Arg Lys Cys Ser Thr Ser Ser
        675             680             685
Leu Leu Glu Ala Cys Thr Phe Arg Arg Pro
    690             695
```